United States Patent [19]

Uchida et al.

[11] 4,366,039

[45] Dec. 28, 1982

[54] OXYGEN SENSING DEVICE HAVING MEANS FOR CONTROL OF CURRENT TO PRODUCE REFERENCE OXYGEN PARTIAL PRESSURE

[75] Inventors: Masaaki Uchida; Hidetoshi Kanegae, both of Yokohama; Shigeo Ishitani, Yokosuka, all of Japan

[73] Assignee: Nissan Motor Company, Limited, Yokohama, Japan

[21] Appl. No.: 238,637

[22] Filed: Feb. 26, 1981

[30] Foreign Application Priority Data

Mar. 3, 1980 [JP] Japan ................................ 55-25212

[51] Int. Cl.³ ............................................ G01N 27/46
[52] U.S. Cl. ................................ 204/195 S; 204/1 T
[58] Field of Search .................. 204/1 S, 195 S, 195 R

[56] References Cited

U.S. PATENT DOCUMENTS

| | | | |
|---|---|---|---|
| 3,129,154 | 4/1964 | Pry | 204/196 |
| 3,208,925 | 9/1965 | Hutchison et al. | 204/196 |
| 4,112,893 | 9/1978 | Anzai | 204/195 S |
| 4,167,163 | 9/1979 | Moder | 204/195 S |
| 4,178,793 | 12/1979 | Bremer et al. | |
| 4,207,159 | 6/1980 | Kimura et al. | 204/195 S |

FOREIGN PATENT DOCUMENTS

2731541  2/1979  Fed. Rep. of Germany .
2750478  5/1979  Fed. Rep. of Germany .
2906459  1/1980  Fed. Rep. of Germany .

*Primary Examiner*—T. Tung
*Attorney, Agent, or Firm*—Schwartz, Jeffery, Schwaab, Mack, Blumenthal & Koch

[57] ABSTRACT

Disclosed is a device useful for detection of air/fuel ratio of an air-fuel mixture subjected to combustion in a combustor by sensing oxygen in the exhaust gas, using a solid electrolyte concentration cell type oxygen-sensitive element which requires supply of a DC current to flow through its solid electrolyte layer between reference and measurement electrode layers to establish a reference oxygen partial pressure at the interface between the reference electrode and the solid electrolyte. The device comprises a control circuit to vary the intensity of the current for the oxygen-sensitive element in dependence on the magnitude of output voltage of the oxygen-sensitive element at least when a predetermined one of said output voltage and a reference voltage is higher than the other in order to compensate variations of the magnitude of the reference oxygen partial pressure caused mainly by variations of the temperature.

12 Claims, 11 Drawing Figures

OXYGEN SENSING DEVICE HAVING MEANS FOR CONTROL OF CURRENT TO PRODUCE REFERENCE OXYGEN PARTIAL PRESSURE

BACKGROUND OF THE INVENTION

This invention relates to a device comprising an oxygen-sensitive element which has an oxygen ion conductive solid electrolyte layer, a reference electrode and a measurement electrode arranged to constitute a concentration cell and a current-supplying circuit to force a DC current to flow through the solid electrolyte layer to cause migration of oxygen ions through this layer from either one of the reference or measurement electrodes toward the other to thereby produce a reference oxygen partial pressure in the element while the measurement electrode is exposed to a gas subject to measurement.

In recent internal combustion engines and particularly in automotive engines, it has become popular to perform feedback control of the air/fuel ratio by utilizing an oxygen sensor installed in an exhaust passage as a device that provides an electrical feedback signal indicative of the air/fuel ratio of an air-fuel mixture actually supplied to the engine. Based on this feedback signal, a control circuit commands a fuel-supplying apparatus such as electronically controlled fuel injection valves to regulate the rate of fuel feed to the engine so as to correct deviations of the actual air/fuel ratio from an intended air/fuel ratio. Usually the oxygen sensor is an oxygen concentration cell utilizing an oxygen ion conductive solid electrolyte, such as zirconia stabilized with calcia or yttria, and there is the need for establishing a reference oxygen partial pressure to enable the oxygen sensor to generate an electromotive force in dependence upon the difference between an oxygen partial pressure in a gas subject to measurement and the reference oxygen partial pressure. It has been a usual practice to utilize either air or a mixture of a certain metal such as nickel and its oxide as the source of oxygen to establish the reference oxygen partial pressure.

U.S. Pat. No. 4,207,159 discloses a new type of oxygen-sensing device which is essentially a combination of an oxygen-sensitive element having a microscopically porous layer of an oxygen ion conductive solid electrolyte with reference and measurement electrode layers formed thereon, a DC power source to force a constant current to flow through the solid electrolyte layer between the two electrode layers and a voltage measuring means to measure an output voltage developed between the two electrode layers of the oxygen-sensitive element. In this device, a reference oxygen partial pressure is established in the oxygen-sensitive element, without using any extra oxygen source material, by a balance between the migration of oxygen ions through the solid electrolyte laser in a definite direction caused by the flow of the aforementioned current and diffusion of oxygen molecules through the porous solid electrolyte layer. Wide applications of this device is expected primarily because of the simplicity of the construction of the oxygen-sensitive element as the result of eliminating the need to use an oxygen source material and the desirability of determining the magnitude of the reference oxygen partial pressure by appropriately determining the intensity of the constant current supplied to the element.

SUMMARY OF THE INVENTION

It is an object of the present invention to provide a device capable of sensing oxygen contained in a gas atmosphere and useful for detecting the air/fuel ratio of an air-fuel mixture subjected to combustion in a combustor, such as a combustion chamber of an internal combustion engine, by sensing oxygen in the combustion gas exhausted from the combustor, which device comprises an oxygen-sensitive element of the above described type and a control circuit which provides a DC current necessary for the oxygen-sensitive element to establish a reference oxygen partial pressure therein and has the function of self-regulating the intensity of the current so as to minimize variations in the output characteristics of the oxygen-sensitive element caused by changes in the temperature of the element.

A device according to the present invention includes an oxygen-sensitive element having an oxygen ion conductive solid electrolyte layer, a reference electrode layer laid on a surface of the solid electrolyte layer and substantially entirely covered with a shield layer and a measurement electrode layer laid on a surface of the solid electrolyte layer and spaced from the reference electrode layer so as to contact a gas subject to sensing. The two electrode layers and at least one of the solid electrolyte layers and the shield layer are microscopically porous and gas-permeable. This element itself is a known one. The device further comprises a control circuit to force a DC current to flow through the solid electrolyte layer in the oxygen-sensitive element between the reference and measurement electrode layers to cause migration of oxygen ions through the solid electrolyte layer from a selected one of the two electrode layers toward the other to thereby establish a reference oxygen partial pressure at the interface between the reference electrode layer and the solid electrolyte layer. A characteristic feature of the present invention, is that the control circuit comprises a comparator means for making a comparison between a predetermined voltage and an output voltage developed between the reference and measurement electrode layers of the oxygen-sensitive element, a multiplier means for multiplying the above-mentioned output voltage by a constant coefficient, and regulation means for regulating the intensity of the above-mentioned DC current by utilizing the outputs of the comparator means and the multiplier means such that the intensity of the current varies in dependence on the magnitude of the above-mentioned output voltage at least when the output of the comparator means indicates that a specific one of the compared voltages is above the other.

The device of the invention is particularly suitable for detection of upward and downward deviations of air/fuel ratio in a combustor from a stoichiometric air/fuel ratio. For this purpose, the intensity of the current for establishing of a reference oxygen partial pressure in the oxygen-sensitive element disposed in the combustion gas is regulated such that the output voltage of the element remains at a considerably high level while the air/fuel ratio is on one side of the stoichiometric point but shifts to a very low level when the air/fuel ratio shifts into the other side of the stoichiometric point, and the output voltage of the element is compared with a reference voltage set at the middle of the high and low levels of the output voltage to ascertain whether the air/fuel ratio is above the stoichiometric ratio or below. For example, when a current is forced to flow in the solid electrolyte layer from the reference electrode toward the measurement electrode, the output voltage remains at a high level while the air/fuel ratio is below the stoichiometric ratio and at a low level while the air/fuel ratio is above the stoichiometric. If, under these circumstances the temperature of the element changes, the high level output voltage tends to exhibit greater fluctuations than the low level output voltage. In this case, the control circuit according to the invention is designed such that the intensity of the current flowing in the oxygen-sensitive element varies depending upon the magnitude of the output voltage of the element in the direction to compensate for predicted fluctuations of the output voltage by the influence of the temperature only when the output voltage is above a predetermined voltage, which may be the same as the above-mentioned reference voltage. This manner of regulation of the current intensity is highly effective for minimizing of the degree of actual fluctuation of the output voltage upon occurrence of a change in the temperature of the element, so that the comparison between the output voltage and the reference voltage for examination of actual air/fuel ratio can be continued with sufficient accuracy even when the oxygen-sensitive element undergoes considerable changes in its temperature.

It is preferable that the control circuit has a peak-voltage holding means for temporarily storing a peak value of the voltage produced by the multiplier means and means for gradually discharging the stored voltage with an adequate time constant for the purpose of avoiding an excessively great change in the current intensity during transition of the output voltage of the oxygen-sensing element from the high level to the low level on the occurrence of a change of the air/fuel ratio across the stoichiometric ratio by utilizing the stored peak voltage as the basis for regulation of the current intensity.

The magnitude of the output voltage of the oxygen-sensitive element depends also on the porosity of the solid electrolyte laser and/or the shield layer, and it is not easy to industrially produce many oxygen-sensitive elements with very small differences in the porosity. When the intensity of the current for establishing a reference oxygen partial pressure is always kept constant, the differences in the porosity become a cause of individually different output characteristics of the industrially produced oxygen-sensitive elements. The regulation of the current intensity by the control circuit according to the invention is also effective for compensation between differences in the porosity. Therefore, the oxygen-sensitive elements used in the devices according to the invention can be produced with less strict control of the porosity of the solid electrolyte layer.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DESCRIPTION OF THE PREFERRED EMBODIMENTS

Figure 1:
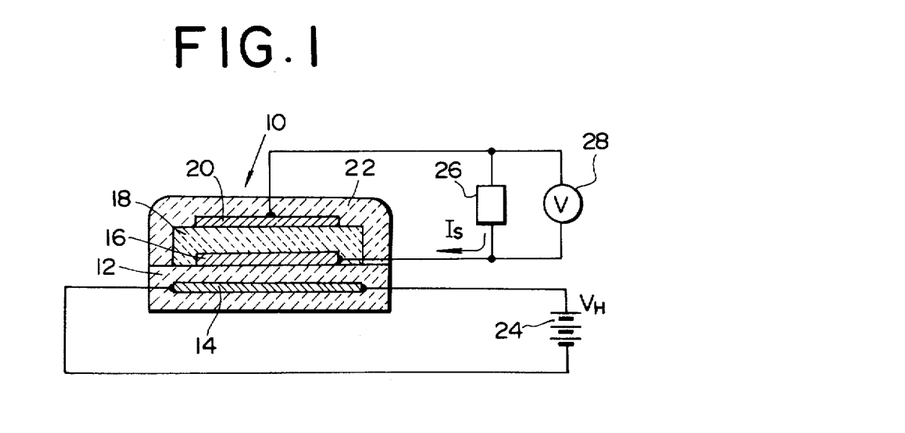
FIG. 1 is a schematic and sectional view of an oxygen-sensing element included in a device according to the present invention.

FIG. 1 shows an exemplary construction of an oxygen-sensitive element 10 for use in the present invention. This element 10 is of the type disclosed in U.S. Pat. No. 4,207,159.

A structurally basic member of this oxygen-sensitive element 10 is a substrate 12 made of an electrochemically inactive ceramic material such as alumina. Usually a heater element 14, for example a thin layer of platinum, is embedded in the substrate 12 because a solid electrolyte used in this element 10 becomes high in its internal resistance and unsatisfactorily low in its activity when the element is not adequately heated; for example when used at temperatures below about 500° C.

An electronically conducting electrode layer 16 called reference electrode layer is formed on a major surface of the substrate 12, and a layer 18 of an oxygen ion conductive solid electrolyte typified by $ZrO_2$ stabilized with CaO or $Y_2O_3$ is formed on the same side of the substrate 12 so as to cover substantially the entire area of the electrode layer 16. Another electronically conducting electrode layer 20 called measurement electrode layer is formed on the outer surface of the solid electrolyte layer 18. Each of these three layers 16, 18, 20 can be formed as a thin, film-like layer (though it may be a "thick layer" in the field of current electronic technology), so that the total thickness of these three layers may become only about 50 microns by way of example. Macroscopically the reference electrode layer 16 is completely shielded from an environmental atmosphere by the substrate 12 and the solid electrolyte layer 18. (Accordingly, the substrate 12 will be called a shield layer in the present specification). However, both the solid electrolyte layer 18 and the measurement electrode layer 20 (the reference electrode layer 16, too) are formed so as to be microscopically porous and permeable to gas molecules. If desired for certain reasons, the shield layer 12 may be made gas-permeably porous instead of, or together with, the solid electrolyte layer 18.

As a modification, it is possible to form both a reference electrode layer and a measurement electrode layer on the same side of the solid electrolyte layer with a suitable distance between the two electrode layers. In that case, a shield layer is formed on the same side of the solid electrolyte layer so as to cover only the reference electrode layer.

Usually the outer surfaces of the measurement electrode layer 20 and the solid electrolyte layer 18, or the entire outer surfaces of the element 10, are covered with a gas-permeably porous protective layer 22 formed of a ceramic material.

In operation, a power supply 24 is connected to the heater 14 in the oxygen-sensitive element 10 to apply a voltage $V_H$ adequate for heating. A current control circuit 26 according to the invention is connected to the reference and measurement electrode layers 16 and 20 of the oxygen-sensitive element 10 to force a DC current $I_S$ of a controlled intensity to flow through the solid electrolyte layer 18 between the two electrode layers 16, 20 to thereby establish a reference oxygen partial pressure at the interface between the reference electrode layer 16 and the solid electrolyte layer 18. The illustrated direction of the flow of the current $I_S$ is exemplary. In parallel with the control circuit 26, a voltage-measuring device 28 is connected to the two electrode layers 16 and 20 to measure an output voltage which is developed between these two electrodes 16 and 20 and indicates the magnitude of an electromotive force generated by an oxygen concentration cell constituted of the two electrode layers 16, 20 and the solid electrolyte layer 18 sandwiched therebetween.

Figure 2:
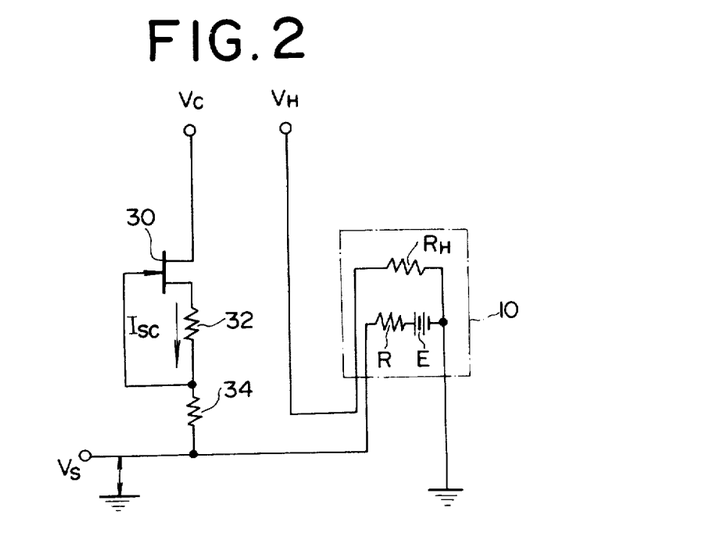
FIG. 2 is a circuit diagram showing a known method of supplying a constant current to the oxygen-sensitive element of FIG. 1.

Heretofore it has been recommended to force a constant current to flow through the solid electrolyte layer 18 in the element 10. FIG. 2 shows an examplary construction of constant current supplying means for this element 10. In this diagram indicated by $R_H$ is the resistance of the heater 14 in FIG. 1, by R is the internal resistance of the element 10 (principally the resistance of the solid electrolyte layer 18), and by E is the electromotive force the element 10 can generate. The constant current circuit utilizes a field effect transistor 30 in the known manner. That is, a source voltage $V_C$ is applied to the drain of the FET 30, while the source side of the FET 30 is connected to the reference electrode layer 16 (or the measurement electrode 20) through a resistor 32 having a suitable resistance $R_S$ and a protective resistor 34. The other electrode layer 20 (or 16) of the element 10 is grounded.

The magnitude of a voltage $V_{GS}$ between the gate and source in this FET 30 is given by:

$$V_{GS} = I_S \times R_S \quad (1)$$

where $I_S$ represents the source current. In this case the voltage $V_{GS}$ is maintained constant, so that a DC current $I_{SC}$ of the same intensity as the source current $I_S$ flows through the solid electrolyte layer 18 in the element 10 to cause migration of oxygen ions in this layer 18 in the direction reverse to the direction of the current flow. By the effect of the oxygen ion migration, a reference oxygen partial pressure can be maintained in the element 10. Therefore, the oxygen concentration cell in the element 10 generates an electromotive force E in dependence on the difference between the reference oxygen partial pressure and an oxygen partial pressure at the measurement electrode layer 20 which contacts a gas subject to measurement, and the element 10 provides an output voltage $V_S$ which is the sum of the electromotive force E and a voltage developed by the flow of the current $I_{SC}$ in the internal resistance R.

The function of the oxygen-sensitive element 10 will be described more in detail to facilitate understanding of the merits of the subsequently described present invention.

Figure 3:
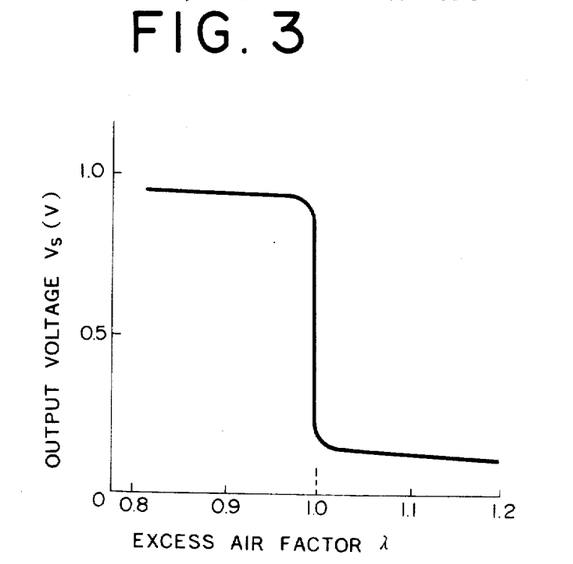
FIG. 3 is a graph showing an example of output characteristics of the oxygen-sensitive element of FIG. 1 when used in exhaust gases discharged from an internal combustion engine.

When the FET 30 in FIG. 2 is connected to the oxygen-sensitive element 10 such that the constant current $I_{SC}$ flows in the solid electrolyte layer 18 from the reference electrode 16 toward the measurement electrode 20, the reference electrode 16 is continuously supplied with oxygen since the current $I_{SC}$ causes oxygen ions to migrate from the measurement electrode 20 toward the reference electrode 16. However, a portion of oxygen accumulated at the reference electrode 16 diffuses into the exterior atmosphere through the porous solid electrolyte layer 18 (or through the shield layer 12 if this layer is made porous), and, as the result of a balance between the supply of oxygen ions and the diffusion of oxygen molecules, the magnitude of oxygen partial pressure at the interface between the reference electrode layer 16 and the solid electrolyte layer 18 is maintained at a nearly constant and relatively high level (for example, of the order of $10^{-1}$ atm). When the oxygen-sensitive element 10 in this state is disposed in a combustion gas such as exhaust gas of an internal combustion engine, on condition that the measurement electrode layer 20 is formed of a catalytic material such as platinum that catalyzes oxidation of hydrocarbons, carbon monoxide, etc. as is usual for this oxygen-sensitive element 10, the output voltage $V_S$ of the element 10 remains at a considerably high level while the excess air factor $\lambda$ of an air-fuel mixture subjected to combustion is smaller than 1.0 (meaning the employment of a fuel-rich mixture), as shown in FIG. 3. When the excess air factor $\lambda$ is greater than 1.0 (meaning the employment of a lean mixture), the magnitude of the output voltage $V_S$ is very small as can be seen in FIG. 3, and there occurs a great and sharp change in the magnitude of the output voltage $V_S$ upon occurrence of a change in the excess air factor $\lambda$ of the mixture across 1.0, i.e. stoichiometric point.

On the contrary, when the FET 30 in FIG. 2 is connected to the element 10 so as to force the constant current $I_{SC}$ to flow in the solid electrolyte layer 18 from the measurement electrode 20 toward the reference electrode 16, there occurs migration of oxygen ions from the reference electrode 16 toward the measurement electrode 20, with the result that a reference oxygen partial pressure produced in this case at the interface between the reference electrode layer 16 and the solid electrode layer 18 remains at a considerably low level (for example, of the order of $10^{-20}$ atm). When the oxygen-sensing element 10 in this state is disposed in the exhaust gas, the relationship between the excess air factor $\lambda$ and the level of the output voltage $V_S$ becomes reverse to that shown in FIG. 3: the output voltage $V_S$ remains at a considerably high level while $\lambda$ is greater than 1.0 and becomes very low when $\lambda$ becomes smaller than 1.0.

In practice, however, there occur considerable changes in the values of the high and low levels of the output voltage $V_S$ mainly by the effect of the temperature of the gas subject to measurement, in either of the above described two cases of the electrical connection for supplying the current $I_{SC}$.

Figure 4:
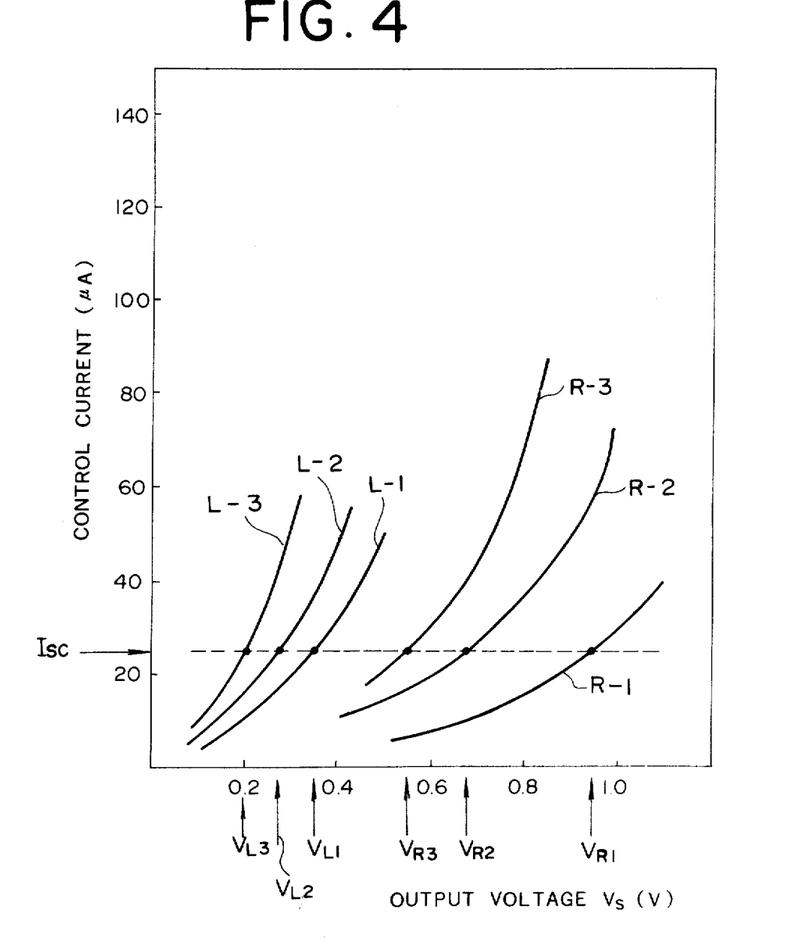
FIG. 4 is a chart showing the dependence of the output voltage of the same oxygen-sensitive element on the temperature, air/fuel ratio in the engine and the intensity of the current supplied to the element.

FIG. 4 illustrates variations in the output voltage $V_S$ in the case of the oxygen-sensitive element 10 being made to exhibit an output characteristic of the type as shown in FIG. 3 by the flow of a current therein from the reference electrode 16 toward the measurement electrode 20. The curve R-1 represents the relationship between the intensity of the current flowing in the element 10 and the magnitude of the output voltage $V_S$ while the element 10 is disposed in an exhaust gas produced by combustion of a slightly rich mixture whose excess air factor $\lambda$ is 0.9 and maintained at a constant temperature of 550° C. This relationship becomes as represented by the curve R-2 when the temperature of the element 10 becomes 650° C. with no change in the value of $\lambda$. If the temperature of the element 10 further rises to 750° C., the current-voltage relationship becomes as represented by the curve R-3 while $\lambda$ is still kept at 0.9. In this chart, the broken line drawn horizontally indicates the intensity of the constant current $I_{SC}$ supplied to the element 10 by the circuit of FIG. 2. Accordingly, the intersection of this line and the curve R-1 gives the magnitude $V_{R1}$ of the output voltage $V_S$ of the element 10 maintained at 550° C. At 650° C., the magnitude of the output voltage $V_S$ becomes $V_{R2}$ that is given by the intersection of the broken line and the curve R-2 despite the constantness of the value (0.9) of $\lambda$, and at 750° C. the output voltage $V_S$ takes a still lowered value $V_{R3}$. As can be seen, changes of practically possible scales in the temperature of the element 10, i.e. exhaust gas temperature, cause great changes in the magnitude of the output voltage $V_S$. Then there arises a difficulty in estimating the air/fuel ratio based on the output of the oxygen-sensing element 10. In the case of utilizing the output characteristic shown in FIG. 3 to ascertain whether the air/fuel ratio is above the stoichiometric point or below, the output voltage $V_S$ is compared with a constant reference voltage set at a value of 0.5–0.6 volts. If the current intensity $I_{SC}$ in FIG. 4 is determined on the premise that the element 10 will be heated to about 550° C. and the reference voltage is set at 0.55 volts, a rise of the temperature to 650° C. or 750° C. by way of example with resultant decrease of the value of the output voltage $V_S$ from $V_{R1}$ to $V_{R2}$ or $V_{R2}$, a value close to 0.55 volts, makes it difficult to correctly estimate whether the value of $\lambda$ is actually smaller than 1.0 or greater.

A principal reason for such lowering of the output voltage $V_S$ with increase in the temperature is that the diffusion of oxygen molecules through the porous solid electrolyte layer 18 augments as the temperature becomes higher, whereby the reference oxygen partial pressure in the element 10 lowers. That is, the difference between the reference oxygen partial pressure and a relatively low oxygen partial pressure in the exhaust gas produced by combustion of a fuel-rich mixture becomes smaller.

Although less significant, the lower level of the output voltage $V_S$ in FIG. 3 also undergoes changes in its numerical value with the temperature of the oxygen-sensitive element 10. In FIG. 4, curves L-1, L-2 and L-3 represent the relationship between the intensity of the current flowing in the element 10 and the output voltage $V_S$ while the element 10 is disposed in an exhaust gas produced by combustion of a slightly lean mixture in which $\lambda$ takes a value of 1.1, at temperatures of 550° C., 650° C. and 750° C., respectively. As the temperature varies within the range of 550°–750° C., the output voltage $V_S$ of the element 10 supplied with the constant current $I_{SC}$ varies between $V_{L1}$ and $V_{L3}$.

Besides the influence of the temperature, the output voltage $V_S$ of the oxygen-sensing element 10 depends on the porosity of the solid electrolyte layer 18 (and/or the shield layer 12 if it is made porous) when operated with the supply of a constant current $I_{SC}$, because the diffusion of oxygen molecules in the porous layer augments as the porosity becomes higher. Therefore, the relationship between the intensity of the current flowing in the element 10 and the output voltage $V_S$ varies as the porosity becomes higher in the same way as the variations caused by changes in the temperature toward the higher side as shown in FIG. 4. From a practical viewpoint, industrially produced oxygen-sensitive elements 10 exhibit some differences in the output voltage $V_S$ from one another because of inevitable differences of the porosity of the solid electrolyte layer 18 in the individual elements 10.

The current control circuit 26 in a device according to the invention has the function of regulating the intensity of the current $I_S$ for establishment of a reference oxygen partial pressure thereby minimizing the degree of the above explained variations in the magnitude of the output voltage $V_S$ of the oxygen-sensitive element 10.

Figure 5:
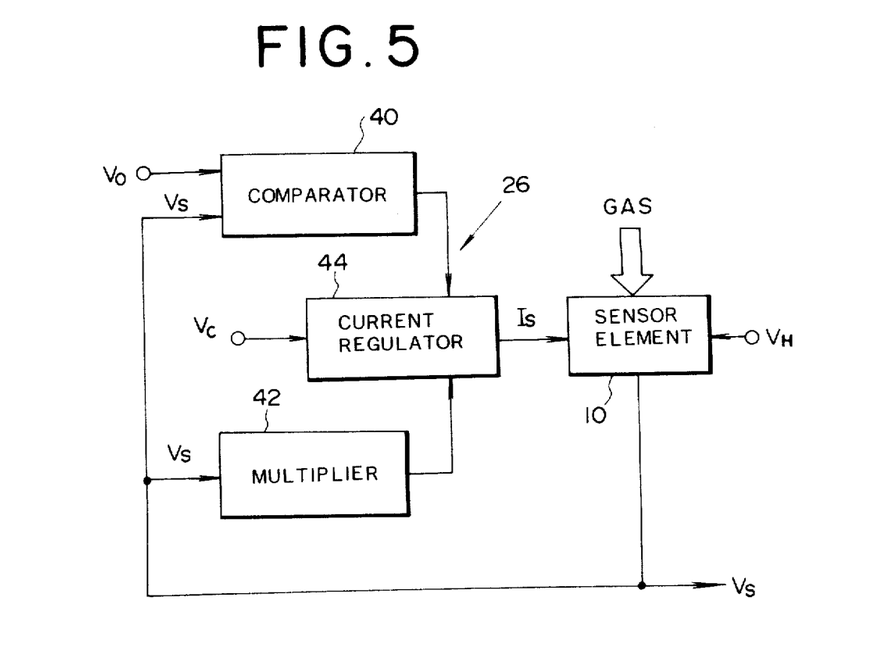
FIG. 5 is a block diagram showing the fundamental construction of a device according to the invention.

As shown in FIG. 5, the current control circuit 26 is fundamentally constituted of a comparator circuit 40 which makes a comparison between the output voltage $V_S$ of the oxygen-sensing element 10 and a predetermined constant voltage $V_O$ and produces a binary signal indicative of the result of the comparison, a multiplier circuit 42 in which the output voltage $V_S$ is multiplied by a constant coefficient M and a current regulation circuit 44 which produces a DC current $I_S$ by utilizing a constant source voltage $V_c$ and regulates the intensity of the current $I_S$ based on the outputs of the comparator circuit 40 and the multiplier circuit 42.

More particularly, when the current $I_S$ flows through the solid electrolyte layer 18 of the oxygen-sensing element 10 from the reference electrode 16 toward the measurement electrode 20 to produce an output characteristic of the type as shown in FIG. 3, the comparator circuit 40 produces a suppression signal whenever the output voltage $V_S$ is lower than the predetermined voltage $V_O$. The suppression signal causes the current regulation circuit 44 to cut off the output of the multiplier circuit 42 and reduce the intensity of the current $I_S$ flowing into the element 10 to a considerably small value, $I_m$, such as a few microamperes. Whenever the output voltage $V_S$ is higher than the predetermined voltage $V_O$, the comparator circuit 40 produces a command signal which causes the current regulation circuit 44 to utilize the output of the multiplier circuit 42 such that the intensity of the current $I_S$ varies in dependence on the value of the output voltage $V_S$: more particularly, the regulation circuit 44 functions to decrease the current $I_S$ as the output voltage $V_S$ augments.

The application of the voltage $V_H$ to the heater 14 in the oxygen-sensitive element 10 is performed in the same manner as in FIG. 2. Of course this heating current circuit is omitted if the element 10 is not provided with any heater.

Figure 6:
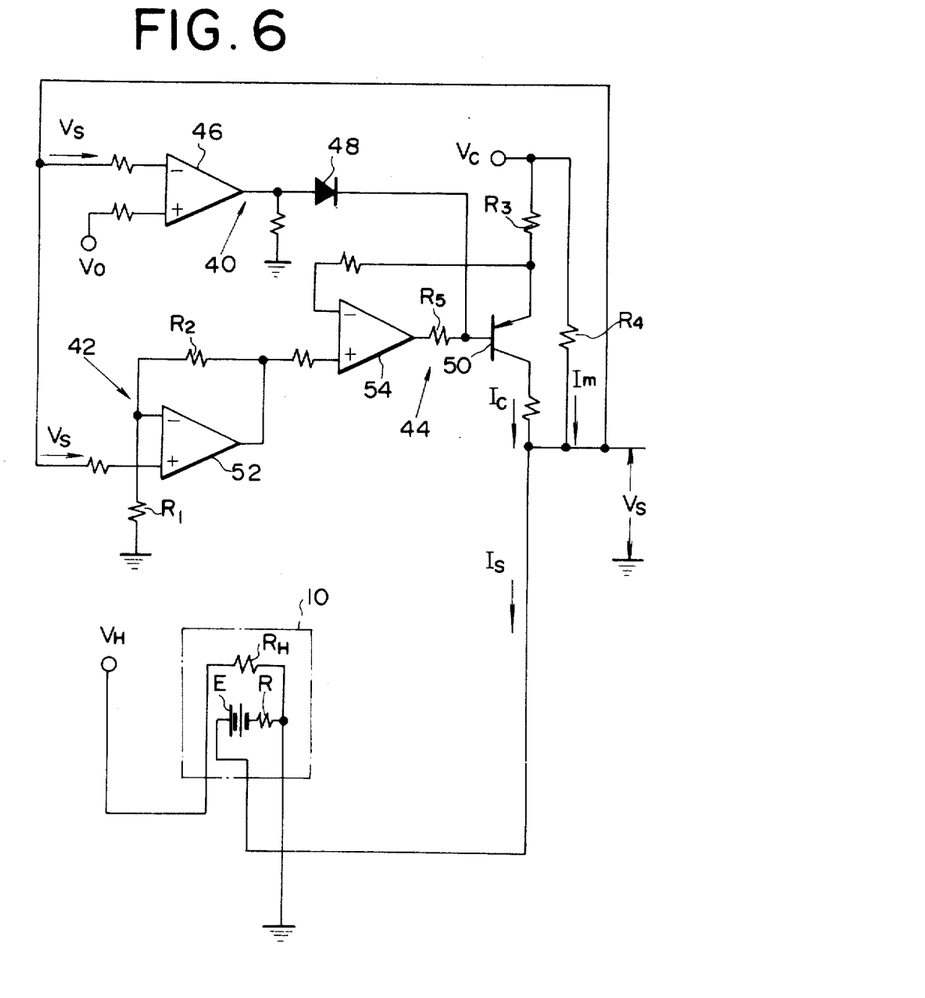
FIG. 6 is a circuit diagram showing an embodiment of a current control circuit in the device of FIG. 5.

FIG. 6 shows a preferred example of actual construction of the control circuit 26 of FIG. 5.

In FIG. 6, an operational amplifier 46 having the function of a comparator and a diode 48 constitute the aforementioned comparator circuit 40. The predetermined voltage $V_O$ and the output voltage $V_S$ of the element 10 are put into the positive and negative input terminals of the operational amplifier 46, respectively, and the output terminal of the operational amplifier 46 is connected to the base of a PNP transistor 50, which is a component of the aforementioned current regulation circuit 44, via the diode 48 connected in the forward direction. An operational amplifier 52 having a multiplying function is the principal component of the multiplier circuit 42. The output voltage $V_S$ of the element 10 is fed the positive input terminal of operational amplifier 52, and a voltage produced by dividing the output voltage of amplifier 52 by two resistances $R_1$ and $R_2$ is fed the negative input terminal. The current regulation circuit 44 includes an operational amplifier 54 whose positive input terminal receives output of the operational amplifier 52. A resistance $R_3$ is connected between the source of the constant voltage $V_c$ and the emitter of transistor 50, and a voltage at the junction between resistance $R_3$ and transistor 50 is fed the negative input terminal of operational amplifier 54. The output terminal of operational amplifier 54 is connected to the base of transistor 50 via a resistance $R_5$, and the collector of transistor 50 is connected to the oxygen-sensitive element 10 so that a collector current $I_C$ of transistor 50 can be supplied to element 10.

While the output voltage $V_S$ of the oxygen-sensitive element 10 is lower than the predetermined voltage $V_O$, the comparator 46 puts out a positive voltage signal which causes transistor 50 to become inoperative, resulting in the interruption of the supply of current through transistor 50 to element 10. However, element 10 is supplied with the aforementioned very small current $I_m$ produced by a resistance $R_4$ connected to the source of the voltage $V_c$ in parallel with the transistor 50. The intensity of this current $I_m$ is given by:

$$I_m = (V_C - V_S)/R_4 \qquad (2)$$

Figure 7:
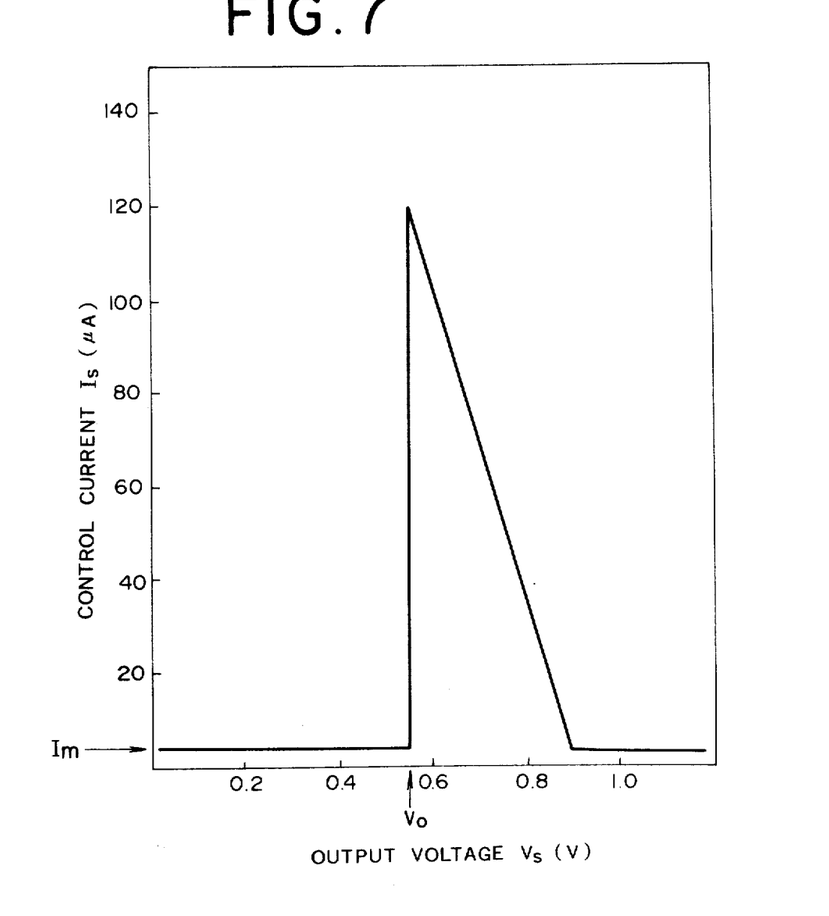
FIG. 7 is a graph showing the relationship between an output voltage of the current control circuit of FIG. 6 and the intensity of a current supplied from this circuit to the oxygen-sensitive element.

As can be seen in FIG. 7, this current $I_m$ is a practically constant current usually smaller than 5 microamperes.

While the output voltage $V_S$ of the element 10 is greater than the voltage $V_O$, the comparator 46 puts out a zero volt signal which renders diode 48 non-conductive, so that transistor 50 becomes conductive. Meanwhile, in operational amplifier 52 the output voltage $V_S$ of the element 10 is multiplied by the constant coefficient M, which is determined by the resistances $R_1$ and $R_2$ as expressed by the following equation:

$$\left(\frac{R_1 + R_2}{R_1}\right) \times V_S = M \cdot V_S \qquad (3)$$

The thus multiplied voltage $M \cdot V_S$ is put into the operational amplifier 54, and the output of this operational amplifier controls the function of the transistor 50 such that the collector current $I_C$ becomes as follows:

$$I_C = (V_C - M \cdot V_S)/R_3 \qquad (4)$$

In this state, the sum of the collector current $I_C$ and the above-described very small current $I_m$ becomes the current $I_S$ that flows through the solid electrolyte layer 18 in the oxygen-sensitive element 10:

$$I_S = I_C + I_m \qquad (5)$$

Then, as can be understood from the equations (4) and (5) and as shown in FIG. 7, the intensity of the current $I_S$ decreases linearly as the difference of the output voltage $V_S$ of the element 10 from the predetermined voltage $V_O$ becomes greater, until the output voltage $V_S$ reaches a value given by $V_C/M$, where the collector current $I_C$ becomes zero. As shown in FIG. 7, in most cases it is suitable to set the constant voltage $V_O$ for use in the comparator 46 at the same value as the reference voltage mentioned hereinbefore in connection with the graph of FIG. 3.

Figure 8:
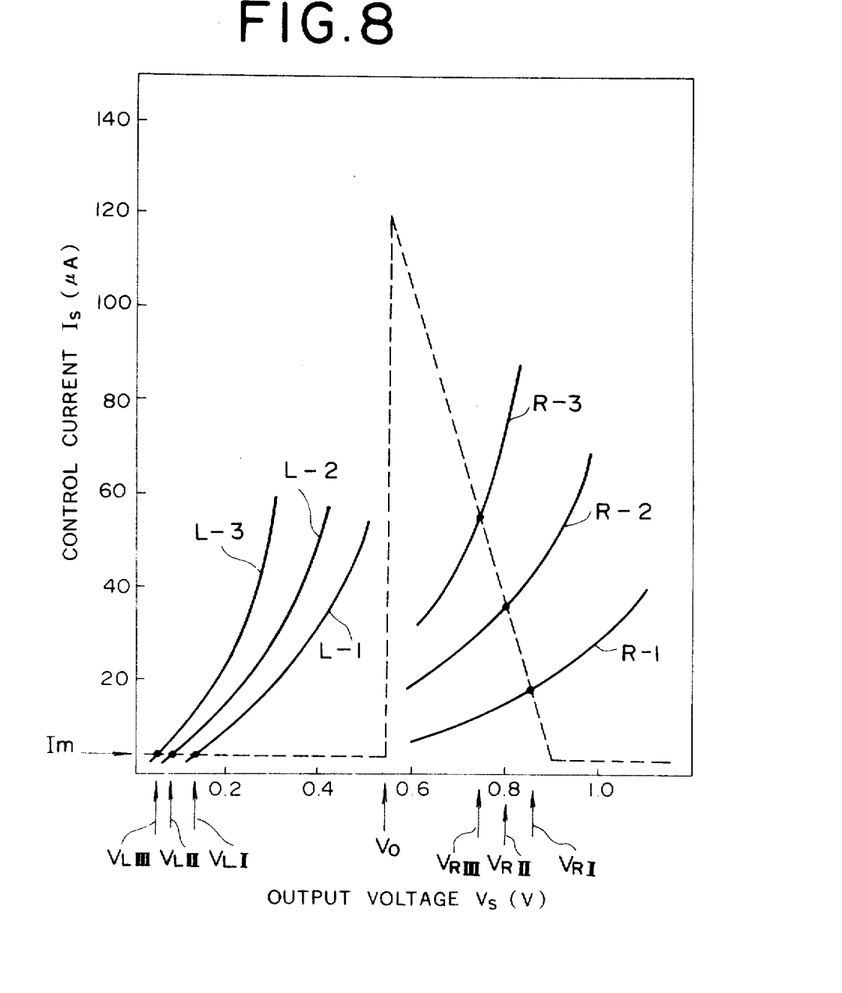
FIG. 8 is a chart showing the effect of operating the oxygen-sensitive element in exhaust gases by using the control circuit of FIG. 6 on the degree of variations in the output voltage of the oxygen-sensitive element with temperature.

FIG. 8 is a chart prepared by superposing FIG. 7 on FIG. 4 to illustrate the effect of regulating the intensity of the current $I_S$ in the manner as shown in FIG. 7.

In the case of combustion of a slightly rich mixture in which excess air factor λ takes a value of 0.9, the output voltage $V_S$ of the oxygen-sensitive element 10 in the exhaust gas becomes higher than the predetermined voltage $V_O$. Accordingly, if the output voltage $V_S$ rises or lowers for any reason the control circuit of FIG. 6 functions to decrease or increase the current $I_S$ in dependence on the rate of the change in the output voltage $V_S$. If the temperature of the element 10 rises, for example, from 550° C. to 650° C. and further to 750° C. there occurs gradual lowering of the output voltage $V_S$ as represented by the curves R-1 R-2 and R-3 despite the maintenance of the constant value of λ. Then the control circuit responds quickly to such lowering of the output voltage $V_S$ by increasing the current $I_S$ as represented by the slant portion of the broken line thereby interrupting the lowering of the output voltage $V_S$. Therefore, the extent of actual lowering of the output voltage $V_S$ becomes very small as can be understood from equilibrated values $V_{RI}$, $V_{RII}$ and $V_{RIII}$ of the output voltage $V_S$ given by the intersections of the slant portion of the broken line and the three curves R-1, R-2 and R-3. The difference between the value $V_{RI}$ at 550° C. and $V_{RIII}$ at 750° C. is only about 0.1 volt, in contrast to the difference of about 0.4 volts between the equilibrated voltage values $V_{R1}$ at 550° C. and $V_{R3}$ at 750° C. shown in FIG. 4. A similar effect can be produced also when the porosity of the solid electrolyte layer and/or shield layer in the element 10 is considerably higher than a standard level.

In the case of combustion of a slightly lean mixture in which λ takes a value of 1.1, the output voltage $V_S$ of the element 10 in the exhaust gas becomes lower than the predetermined voltage $V_O$. Accordingly, only the very small current $I_m$ is supplied to the element 10. Since this current $I_m$ is considerably smaller than the constant current $I_{SC}$ shown in FIG. 4, the extent of fluctuation of the output voltage $V_S$ attributed to a change in the temperature between 550° C. and 750° C. becomes appreciably smaller than in the case of FIG. 4. In the example shown in FIG. 8, the difference between an output voltage value $V_{LI}$ at 550° C. and a smaller value $V_{LIII}$ at 750° C. is only about 0.1 volt, but in FIG. 4 the difference between the corresponding two values $V_{L1}$ and $V_{L3}$ is greater than 0.15 volts.

Thus, the above described control circuit has the capability of appreciably stablizing the output voltage $V_S$ of the element 10 at each of its high and low output levels and preventing the output voltage $V_S$ from becoming close to a reference voltage set at a value between the two output levels even though the element 10 undergoes considerable changes in its temperature. Accordingly, when the device according to the invention is used to examine whether actual air/fuel ratio in a combustor is above a stoichiometric ratio or below, always the examination can easily be carried out with remarkably improved accuracy.

The device according to the invention is expected to be used mainly in apparatus for feedback control of air/fuel ratio in automotive internal combustion engines. In many cases the aim of the feedback control is to maintain the excess air factor λ of an air-fuel mixture at 1.0, that is, to feed the engine with a stoichiometric mixture. However, it is practically impossible to stably maintain an exactly stoichiometric condition: it is inevitable that a slightly rich mixture (λ<1) and a slightly lean mixture (λ>1) are alternately supplied to the engine at a relatively high frequency. When the oxygen-sensitive element 10 disposed in the exhaust gas exhibits an output characteristic of the type as shown in FIG. 3, there occurs abrupt transition of the output voltage $V_S$ from the high level to the low level or reversely each time the value of λ changes across 1.0. As the intensity of the current $I_S$ supplied to the element 10 is controlled in the manner as illustrated in FIG. 7, each time when the output voltage $V_S$ shifts from the high level to the low level there occurs a quick and great increase in the intensity of the current $I_S$. The increase of the current $I_S$ at this instant is undesirable because it is obstructive to smooth and quick drop of the output voltage $V_S$ to the low level in FIG. 3, although the increased current $I_S$ will soon drop to the very small current $I_m$ when the output voltage $V_S$ becomes below $V_O$, and also because the element 10 might be deteriorated by the supply of excessively augmented current $I_S$ (in the case of the control characteristic of FIG. 7, the maximum value of the current $I_S$ reaches about 120 microamperes).

Figure 9:
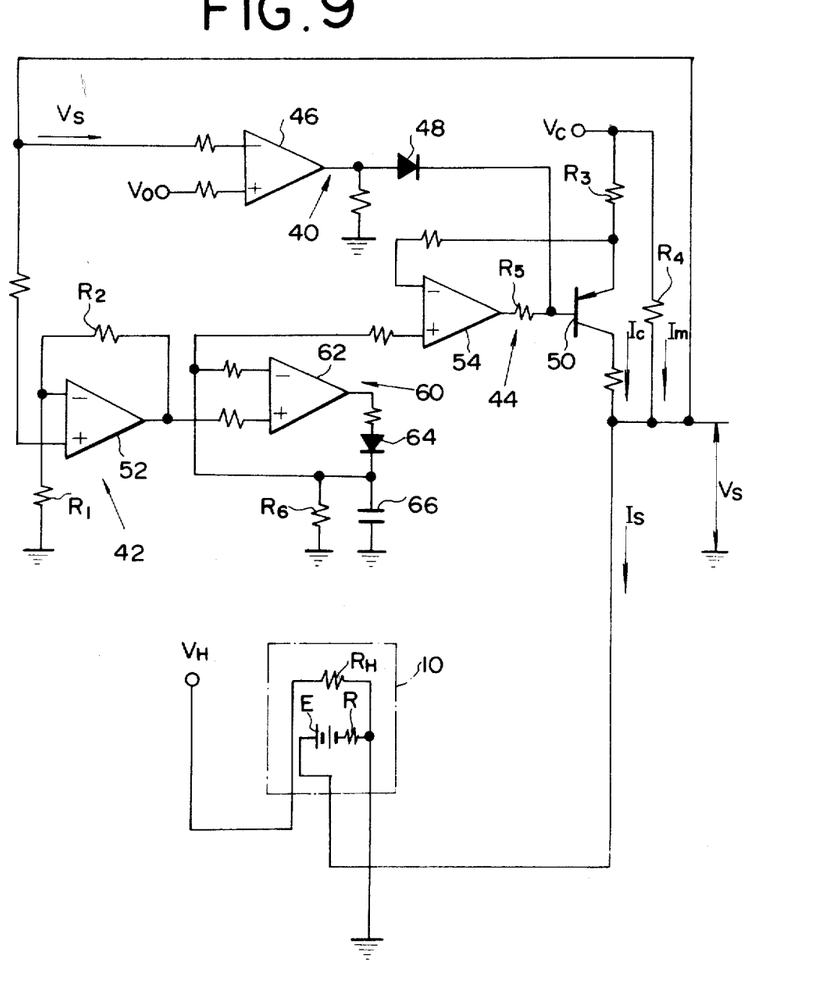
FIG. 9 is a circuit diagram showing a modification of the control circuit of FIG. 6.

To avoid a great augmentation of the current $I_S$ during transition of the output voltage $V_S$ of the element 10 from the high level to the low level, it is preferable to add a peak-voltage holding circuit to the current regulation circuit 44 or the multiplier circuit 42 in the control circuit of FIG. 6 in order to temporarily store a maximal value of the multiplied output voltage M $V_S$ and utilize it as the basis for regulation of the intensity of the current $I_S$. FIG. 9 shows the addition of a peak-voltage holding circuit 60 to the control circuit of FIG. 6 as an example.

The peak-voltage holding circuit 60 has an operational amplifier 62 which receives the output of the multiplier 52 at its positive input terminal. The output terminal of the operational amplifier 62 is connected to a capacitor 66 via a diode 64, and a resistance $R_6$ is connected in parallel with the capacitor 66. The positive input terminal of the operational amplifier 54 of the current regulation circuit 44 is connected to the junction between the diode 64 and the capacitor 66. Otherwise the circuit of FIG. 9 is identical with that of FIG. 6.

This circuit 60 stores a maximal value of the voltage M·$V_S$ provided by the multiplier 52 and gradually discharges the stored voltage at a rate determined by a time constant given by $R_6 \times C_1$, where $C_1$ represents the capacitance of the capacitor 66. Since M is a constant, it may be said that this circuit 60 modifies the voltage M·$V_S$ to a peak voltage $V_P$ which is proportional to a maximal value $V_{max}$ of the output voltage $V_S$ of the oxygen-sensitive element 10:

$$V_P = M \cdot V_{max} \tag{6}$$

The current regulation circuit 44 utilizes this peak voltage $V_P$ in place of the voltage M $V_S$ in regulating the collector current $I_C$ in the way as described with reference to FIG. 6. Therefore, $$I_C = (V_C - V_P)/R_1 \tag{7}$$

While the output voltage $V_S$ of the element 10 is lower than the predetermined voltage $V_O$, only the very small current $I_m$ is supplied to the element 10. While the output voltage $V_S$ is greater than the voltage $V_O$, a current expressed by $I_c + I_m = I_s$ is supplied to the element 10.

In the cases of air/fuel ratio control for automotive internal combustion engines, it is suitable to set the time constant $R_6 \times C_1$ at a value in the range from about 5 sec to about 15 sec. Usually an abrupt drop of the output voltage $V_S$ of the element 10 in response to an abrupt shift of a rich mixture to a lean mixture in the engine is completed within 0.5 seconds. In practice, however, it is desirable to determine the time constant with sufficient allowance because the response time of the element 10 varies by various reasons including aging of the element 10 and differences in characteristics of industrially produced elements. This is permissible because changes in the output voltage $V_S$ by the influence of temperature occur relatively slowly. However, if the time constant is made unduly long it becomes impossible to compensate lowering of the output voltage $V_S$ when significant lowering of the reference oxygen partial pressure occurs within a relatively short period of time.

Figure 10:
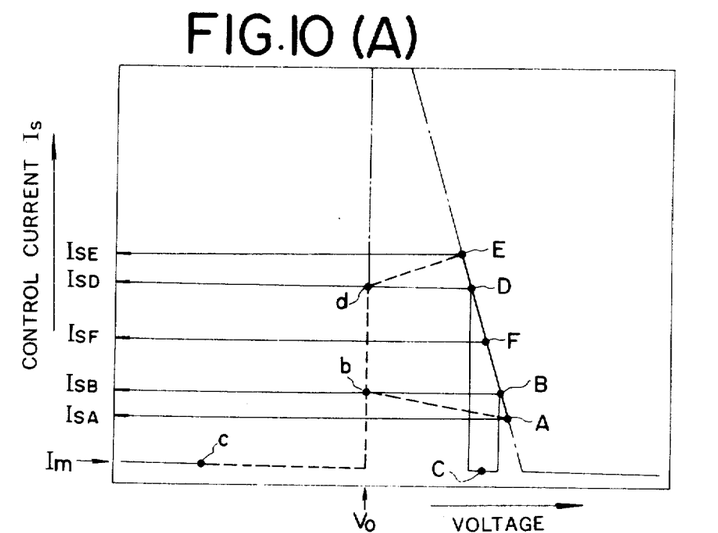
FIGS. 10(A) and 10(B) are charts for the explanation of the function of the control circuit of FIG. 9.

FIGS. 10(A) and 10(B) illustrate the manner of changes in the above described voltages $V_S$ and $V_P$ and the intensity of the current $I_S$ actually supplied to the oxygen-sensitive element 10 when the device according to the invention including the control circuit of FIG. 9 is used in a feedback air/fuel ratio control system for an automotive internal combustion engine with the aim of maintaining a stoichiometric condition of the air-fuel mixture. The current $I_S$ is forced to flow from the reference electrode 16 in the element 10 toward the measurement electrode layer 20 so that the output characteristic of the element 10 is as shown in FIG. 3. In FIG. 10(B), the curve in solid line represents the peak voltage $V_P$ (which attenuates at a rate determined by the time constant $R_6 \times C_1$) by the values of a modified voltage $V_P'$ given by $$V_P' = V_P/M \tag{8}$$

Since $V_P$ is based on the multiplication of the output voltage $V_S$ by the constant M, the employment of the modified form $V_P'$ allows the curve to partly overlap the curve (in broken line) representing the output voltage $V_S$ and accordingly facilitates to present understandable explanation.

While the engine is fed with a slightly rich mixture (λ<1) the output voltage $V_S$ of the element 10 remains at the maximally high level in FIG. 3, so that the voltage $V_P'$ temporarily stored in the peak-voltage holding circuit 60 agrees with $V_S$. In this state, the current $I_S$ supplied to the element 10 is of a relatively low intensity $I_{SA}$ corresponding to the point A in FIGS. 10(A) and 10(B). During an abrupt shift of the rich mixture to a slightly lean mixture (λ>1) the output voltage $V_S$ exhibits a sharp drop as shown in FIG. 10(B), but the peak voltage $V_P'$ stored in the circuit 60 undergoes a gradual lowering to reach a value corresponding to point B in the charts when the output voltage $V_S$ reaches the predetermined voltage $V_O$. At this stage, therefore, the current $I_S$ increases from $I_{SA}$ toward $I_{SB}$. When the output voltage $V_S$ becomes below the voltage $V_O$ the comparator 46 puts out the suppression signal, with the result that the intensity of the current to the element 10 abruptly drops from $I_{SB}$ (corresponding to points b and B where $V_S = V_O$) to the very small value $I_m$. When the lean mixture is again changed to a slightly rich mixture ($\lambda < 1$) there occurs a sharp rise of the output voltage $V_S$, but at this stage the attenuating voltage $V_P'$ is still higher than the output voltage $V_S$. The very small current $I_m$ is maintained until the output voltage $V_S$ rises to the level of the voltage $V_O$ at the point d. As the output voltage $V_S$ exceeds the voltage $V_O$, the current regulation circuit 44 begins to utilize the output of the peak-voltage holding circuit 60 to result in a sudden increase of the current intensity from $I_m$ to $I_{SD}$. Thereafter the current intensity increases gradually to $I_{SE}$ corresponding to a point E where the output voltage $V_S$ becomes equal to the attenuating voltage $V_P'$. As the output voltage $V_S$ further rises accompanied by a corresponding rise of the voltage $V_P'$ toward points F and A, the current intensity decreases gradually from $I_{SE}$ to $I_{SF}$ and further to the initial value $I_{SA}$.

Thus, the use of the voltage $V_P$ provided by the peak-voltage holding circuit 60 prevents the current $I_S$ from increasing beyond a permissible value such as $I_{SE}$ during transition of the output voltage $V_S$ from the high level to the low level.

In the foregoing description of the illustrated embodiments the output characteristic of the oxygen-sensitive element 10 was assumed to be as shown in FIG. 3. However, these embodiments are similarly effective also when the element 10 exhibits the reverse output characteristic to produce a high level output in a combustion gas produced from a lean air-fuel mixture.

The value of the predetermined voltage $V_O$ needs not to be exactly agree with the mean value of the high and low levels of the output voltage $V_S$ of the element 10. Furthermore, it is permissible and sometimes even preferable to make this voltage $V_O$ variable. Because of an inevitable fact that the internal resistance R of the solid electrolyte 18 increases as the temperature of the element 10 lowers, the rise of the output voltage $V_S$ caused by lowering of the temperature of the element 10 is further enhanced by an increase in the voltage value given by $R \times I_S$. Therefore, if the voltage $V_O$ is kept constant sometimes it will be possible that even the low level of the output voltage $V_S$ of the element 10 exhibiting an output characteristic of the type shown in FIG. 3 becomes very close to or above the predetermined voltage $V_O$. When the present invention is applied to an automotive engine, it is desirable to adjust the value of the voltage $V_O$ according to operating conditions of the engine. For example, the voltage $V_O$ would be made relatively high during idling of the engine and relatively low during running of the car, and/or the voltage $V_O$ would be made relatively high during operation of the engine under low-load conditions and relatively low under high-load conditions.

In the above described embodiments, the control circuit 26 works such that the current $I_S$ undergoes a linear increase or decrease so long as the output voltage $V_S$ lowers or rises within the range from $V_O$ to a higher voltage determined by $V_c/M$. However, such a control characteristic is exemplary and is not limitative. The control circuit 26 may alternatively be designed so as to vary the intensity of the current $I_S$ either stepwise or according to a quadric function.

The foregoing description of the preferred embodiments of the invention have been prepared for purposes of illustration and description. They are not intended to be exhaustive or to limit the invention to the precise forms disclosed, and obviously many modifications and variations are possible in light of the above teaching. The embodiments were chosen and described in order to best explain the principle of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A device for sensing oxygen contained in a gas atmosphere comprising:
   (1) an oxygen-sensitive element having an oxygen ion conductive solid electrolyte layer, a reference electrode layer laid on a surface of said solid electrolyte layer and substantially entirely covered with a shield layer and a measurement electrode layer laid on a surface of said solid electrolyte layer and spaced from said reference electrode layer so as to contact a gas subject to sensing, said reference and measurement electrode layers and at least one of said solid electrolyte layer and said shield layer being microscopically porous and gas-permeable; and
   (2) a control circuit electrically connected to said oxygen-sensitive element to cause a DC control current, to flow through said solid electrolyte layer between said reference and measurement electrode layers to cause migration of oxygen ions through said solid electrolyte layer from selected one of said reference and measurement electrode layers toward the other to thereby establish a reference oxygen partial pressure at the interface between said reference electrode layer and said solid electrolyte layer, the control circuit comprising:
      (a) comparator means for comparing a reference voltage and an output voltage developed between said reference and measurement electrode layers of said element;
      (b) multiplier means for multiplying said output voltage by a constant coefficient; and
      (c) regulation means for regulating the intensity of said control current by utilizing the outputs of said comparator means and said multiplier means whereby the intensity of said control current varies depending upon the magnitude of said output voltage when the output of said comparator means indicates a predetermined one of the compared two voltages is higher than the other.

2. A device according to claim 1, wherein said regulation means is operable to decrease said control current as said output voltage rises and increase said control current as said output voltage lowers while the output of said comparator means indicates that said output voltage is higher than said reference voltage.

3. A device according to claim 2, wherein said regulation means is operable to maintain the intensity of said control current substantially constant while the output of said comparator means indicates that said output voltage is lower than said reference voltage.

4. A device according to claim 3, wherein said regulation means regulates the intensity of said control current within a range whereby, when said oxygen-sensitive element is disposed in a combustion gas discharged from a combustor which is fed with an air-fuel mixture, said output voltage remains at a maximally high level so long as the air/fuel ratio of said air-fuel mixture remains on one side of a stoichiometric air/fuel ratio but shifts to a minimally low level when the air/fuel ratio is on the other side of the stoichiometric air/fuel ratio.

5. A device according to claim 4, wherein said control circuit further comprises a peak-voltage holding means for temporarily storing a maximal value of a voltage produced by said multiplier means and gradually discharging the stored voltage, said peak-voltage holding means being connected to said regulation means such that said control current is increased in dependence on the magnitude of the voltage retained in said peak-voltage holding means while the output of said comparator means indicates that said output voltage is higher than said reference voltage.

6. A device according to claim 4, wherein said regulation means comprises a transistor connected to a DC power source and said oxygen-sensitive element such that a collector current of said transistor is supplied to said element while said transistor is in a conducting state, a resistance connected to said power supply and said element in parallel with said transistor, and an operational amplifier having an input terminal connected to the output terminal of said multiplier means and an output terminal connected to the base of said transistor, the output terminal of said comparator means being connected to a junction between said operational aplifier and the base of said transistor such that said transistor becomes nonconducting while the output of said comparator means indicates that said output voltage is lower than said reference voltage but becomes conducting and operative such that the intensity of said collector current varies in dependence on the magnitude of the voltage produced by said multiplier means while the output of said comparator means indicates that said output voltage is higher than said reference voltage.

7. A device according to claim 6, wherein said collector current varies proportionally to the difference between the voltage of said power source and the voltage produced by said multiplier means.

8. A device according to claim 4, wherein said regulation means comprises a transistor connected to a DC power source and said oxygen-sensitive element such that a collector current of said transistor is supplied to said element while said transistor is in conducting state, a resistor connected to said power source and said element in parallel with said transistor, and a first operational amplifier with its output terminal connected to the base of said transistor, said control circuit further comprising a peak-voltage holding means including a grounded capacitor, a resistance grounded in parallel with said capacitor and a second operational amplifier having an input terminal connected to the output terminal of said multiplier means and an output terminal connected to said capacitor such that a maximal value of the voltage produced by said multiplier means is charged in said capacitor and gradually discharged, said first operational amplifier having an input terminal connected to a junction between said output terminal of said second operational amplifier and said capacitor, the output terminal of said comparator means being connected to a junction between said first operational amplifier and the base of said transistor such that said transistor becomes nonconducting while the output of said comparator means indicates that said output voltage is lower than said reference voltage but becomes conducting and operative such that the intensity of said collector current varies in dependence on the magnitude of the voltage retained in said peak-voltage holding means while the output of said comparator means indicates that said output voltage is higher than said reference voltage.

9. A device according to claim 8, wherein said collector current varies proportionally to the difference between the voltage of said power source and the voltage retained in said peak-voltage holding means.

10. A device according to claim 1, wherein said control current flows in said solid electrolyte layer from said reference electrode layer toward said measurement electrode layer.

11. A device according to claim 1, wherein said reference and measurement electrode layers are formed on the two opposite surfaces of said solid electrolyte layer, respectively.

12. A device according to claim 1, wherein said oxygen-sensitive element includes an electric heater means.

* * * * *